US012773403B2

(12) United States Patent
Ogawa et al.

(10) Patent No.: US 12,773,403 B2
(45) Date of Patent: Oct. 27, 2026

(54) SCOPOLAMINE COMPOSITIONS AND TRANSDERMAL PATCHES MADE THEREFROM

(71) Applicants: NOBELPHARMA CO., LTD., Tokyo (JP); YUTOKU PHARMACEUTICAL INDUSTRIES CO., LTD., Kashima (JP)

(72) Inventors: Takayuki Ogawa, Kashima (JP); Kenta Nishimura, Kashima (JP); Hiroaki Ueno, Kashima (JP); Yuhei Tani, Kashima (JP)

(73) Assignees: NOBELPHARMA CO., LTD., Tokyo (JP); YUTOKU PHARMACEUTICAL INDUSTRIES CO., LTD., Kashima (JP)

( * ) Notice: Subject to any disclaimer, the term of this patent is extended or adjusted under 35 U.S.C. 154(b) by 927 days.

(21) Appl. No.: 17/440,416

(22) PCT Filed: Mar. 6, 2020

(86) PCT No.: PCT/JP2020/009575

§ 371 (c)(1),
(2) Date: Sep. 17, 2021

(87) PCT Pub. No.: WO2020/189323

PCT Pub. Date: Sep. 24, 2020

(65) Prior Publication Data

US 2022/0160697 A1 May 26, 2022

(30) Foreign Application Priority Data

Mar. 19, 2019 (JP) ................................ 2019-050914

(51) Int. Cl.
*A61K 31/46* (2006.01)
*A61K 47/32* (2006.01)

(52) U.S. Cl.
CPC .............. *A61K 31/46* (2013.01); *A61K 47/32* (2013.01)

(58) Field of Classification Search
CPC ................................ A61K 31/46; A61K 47/32
See application file for complete search history.

(56) References Cited

U.S. PATENT DOCUMENTS

| | | | |
|---|---|---|---|
| 4,832,953 | A | 5/1989 | Campbell et al. |
| 5,714,162 | A | 2/1998 | Muller |
| 6,620,429 | B1 | 9/2003 | Müller |
| 2001/0006628 | A1 | 7/2001 | Govil et al. |
| 2002/0150613 | A1 | 10/2002 | Govil et al. |
| 2009/0299304 | A1 | 12/2009 | Tang |

FOREIGN PATENT DOCUMENTS

| | | | |
|---|---|---|---|
| CN | 1994307 | A | 7/2007 |
| CN | 101669917 | A | 3/2010 |
| JP | 1-203320 | A | 8/1989 |
| JP | 9-48726 | A | 2/1997 |
| JP | 10-182436 | A | 7/1998 |
| JP | 11-60475 | A | 3/1999 |
| JP | 2002-255797 | A | 9/2002 |
| JP | 4081139 | B2 | 4/2008 |
| JP | 2009-528357 | A | 8/2009 |
| JP | 4466977 | B2 | 5/2010 |
| JP | 2015-083569 | A | 4/2015 |
| JP | 5695562 | B2 | 4/2015 |
| WO | 96/20699 | A1 | 7/1996 |
| WO | 2007/100757 | A2 | 9/2007 |
| WO | 2009/158120 | A2 | 12/2009 |

OTHER PUBLICATIONS

Berge et al. (J. of Pharmaceutical Sci. vol. 66, No. 1, Jan. 1977) (Year: 1977).*
Jung (J. Kor. Pharm. Sci., vol. 33, No. 2, 141-144 (2003)) (Year: 2003).*
Bosman (International Journal of Pharmaceutics 169 (1998) 75-82) (Year: 1998).*
Extended European Search Report dated Dec. 1, 2022 in Application No. EP 20 77 2846.0.
International Search Report for PCT/JP2020/009575 dated May 19, 2020 (PCT/ISA/210).

* cited by examiner

*Primary Examiner* — Kortney L. Klinkel
*Assistant Examiner* — Richard Grant Peckham
(74) *Attorney, Agent, or Firm* — Sughrue Mion, PLLC

(57) ABSTRACT

A medicinal composition containing a scopolamine salt and/or a hydrate thereof, polyvinylpyrrolidone, and a base. The medicinal composition is excellent in terms of absorption of the drug into the living body and chemical stability thereof.

6 Claims, No Drawings

SCOPOLAMINE COMPOSITIONS AND TRANSDERMAL PATCHES MADE THEREFROM

CROSS REFERENCE TO RELATED APPLICATIONS

This application is a National Stage of International Application No. PCT/JP2020/009575 filed Mar. 6, 2020, claiming priority based Japanese Patent Application No. 2019-050914 filed Mar. 19, 2019.

TECHNICAL FIELD

The present invention relates to a pharmaceutical composition containing a scopolamine salt and/or its hydrate as an active ingredient.

BACKGROUND ART

Scopolamine is widely known as an anticholinergic agent and is a drug with effects such as suppression of oral and respiratory secretions and prevention of adverse parasympathetic reflexes. Pharmaceutical products containing scopolamine as an active ingredient have been developed. For example, "HYSCO (registered trademark) Subcutaneous Injection, Kyorin Pharmaceutical," which is an injection containing scopolamine hydrobromide hydrate as an active ingredient, and "Transderm Scop (registered trademark), Novartis," which is a patch containing scopolamine free base as an active ingredient, are produced and marketed in Japan and abroad, respectively.

As is widely known, there is a lipid bilayer around the cell, which acts as a barrier to restrict the permeability to substances inside and outside the cell. Of course, the lipid bilayer is hardly permeable to water-soluble substances and highly permeable to lipophilic substances. Thus, in general, drugs with higher lipophilicity are more likely to be absorbed into cells and enter the blood than drugs with higher water solubility, except for injection drugs that can avoid the barrier function of the body, such as mucous membranes with a lipid bilayer or epidermis. Scopolamine hydrobromide hydrate, a scopolamine salt, is highly soluble in water and must be a highly lipophilic free base in order to enter cells. However, it is generally preferred that the drug is in the form of salt from handling and chemical stability. In the present description, the term "chemical stability" indicates stability with respect to the decomposition of a compound, and the term "physical stability" indicates stability with respect to the crystal precipitation of a compound.

When attempting to produce a pharmaceutical composition containing scopolamine hydrobromide hydrate, which is a scopolamine salt, the inventors have found that a pharmaceutical composition having excellent chemical stability but low absorption into the living body can be obtained, while when attempting to produce a pharmaceutical composition using scopolamine hydrobromide hydrate as a free base during production or in a pharmaceutical composition, the inventors have found a pharmaceutical composition having excellent absorption into the living body but low chemical stability. Further, repeated studies by the inventors demonstrated that optical isomers of scopolamine and aposcopolamine are the main decomposition products in the decomposition of scopolamine in the pharmaceutical composition.

With regard to the technology related to the absorption in the living body and chemical stability of scopolamine, for example, Patent Document 1 discloses a method for improving the absorption of scopolamine in the living body without deteriorating the chemical stability by using an absorption promoter other than acid in a composition containing a compound that causes a decomposition reaction using acid as a catalyst. However, there is no description of how to resolve the deterioration of chemical stability due to factors other than acid.

Patent Document 2 shows a method for improving the absorption of scopolamine into a living body without deteriorating the chemical stability and physical stability of scopolamine by using a composition that does not contain vinyl acetate and a polar component but does not describe a method for solving the deterioration of the chemical stability of a composition containing a polar component. When a scopolamine salt is used because of handling and chemical stability, in order to obtain a pharmaceutical composition having an excellent absorption of scopolamine into a living body, it is necessary to include a base which is a polar component to make the scopolamine salt a scopolamine free base during production or in the pharmaceutical composition, and therefore the method of the patent is not applicable.

Patent Documents 3, 4, and 5 disclose methods for improving the physical stability of scopolamine to maintain or improve its absorption into a living body but do not suggest methods for improving its chemical stability.

PRIOR ART DOCUMENT

Patent Documents

Patent Document 1: Japanese Patent No. 4081139
Patent Document 2: Japanese Unexamined Patent Application Publication (Translation of PCT Application) No. 2009-528357
Patent Document 3: U.S. Pat. No. 4,832,953
Patent Document 4: Japanese Patent No. 4466977
Patent Document 5: Japanese Patent No. 5695562

DISCLOSURE OF THE INVENTION

Problems to be Solved by the Invention

The present invention has been made in view of the above problems, and the present invention intends to provide a pharmaceutical composition containing a scopolamine salt and/or a hydrate thereof, which has high absorption of scopolamine into a living body and is also excellent in chemical stability of scopolamine.

Means for Solving the Problem

Repeated studies conducted by the inventors in order to solve the above-mentioned problems demonstrated that including polyvinylpyrrolidone in a pharmaceutical composition in which a scopolamine salt and/or a hydrate thereof is used as a free base during production or in a pharmaceutical composition maintains high absorption of scopolamine into the living body and improves chemical stability. As described in the above Patent Document 5, polyvinylpyrrolidone improves the physical stability of scopolamine. In general, the dissolved state and the amorphous state are chemically unstable compared to the crystalline state. Therefore, including polyvinylpyrrolidone in the pharmaceutical composition is considered disadvantageous in the chemical stability of scopolamine. Hydroxypropyl cellulose, which is known to improve the physical stability of scopolamine in the same manner as polyvinylpyrrolidone described in Patent Document 5, has no effect of improving the chemical stability of scopolamine by being contained in the pharmaceutical composition, and conversely, the chemical stability of scopolamine is lowered. Surprisingly, however, including polyvinylpyrrolidone in the pharmaceutical composition improves the chemical stability of scopolamine and suppresses the generation of both optical isomers of scopolamine and aposcopolamine, which are the main decomposition product. Furthermore, the inventors have demonstrated that the chemical stability of scopolamine is further improved by using an amine compound as a base for making a scopolamine salt and/or its hydrate a free base during manufacture or in a pharmaceutical composition. Specifically, including polyvinylpyrrolidone in a composition containing a scopolamine salt and/or a hydrate thereof and using an amine compound as a base for making the scopolamine salt and/or hydrate a free base make it possible to obtain a pharmaceutical composition having high scopolamine absorption into the living body and having improved chemical stability of scopolamine, and thus the present invention has been completed.

Advantageous Effects of Invention

The pharmaceutical composition of the present invention (hereinafter referred to as the "composition of the present invention") has high absorption of scopolamine into the living body, and since the decomposition of scopolamine is effectively suppressed, the pharmacological effect of scopolamine can be effectively and continuously utilized The composition of the present invention is a pharmaceutical composition containing a salt of scopolamine ((−)-(S)-3-hydroxy-2-phenylpropionic acid (1R, 2R, 4S, 7S, 9S)-9-methyl-3-oxa-9-azatricyclo [3.3.1.0 2,4] non-7-yl ester) which is an active ingredient, and/or a hydrate thereof, polyvinylpyrrolidone and a base.

Examples of the salts of scopolamine used in the composition of the present invention include acid addition salts with inorganic acids or organic acids and include, but are not limited to, hydrochloride, hydrobromide, nitrate, phosphate, sulfate, acetate, ascorbate, benzoate, cinnamate, citrate, formate, fumarate, glutamate, lactate, maleate, malate, malonate, mandelate, methanesulfonate (mesylate), phthalate, salicylate, stearate, succinate, tartrate, propionate, butyrate, pamoate, p-toluenesulfonate (tosylate), and the like. It is favorable to use scopolamine hydrobromide and/or scopolamine hydrobromide hydrate in the composition of the present invention.

The composition of the present invention may contain a therapeutically effective amount of a scopolamine salt and/or a hydrate thereof, and the state thereof is not particularly limited, but a dissolved or amorphous state is preferred from the viewpoint of absorption into a living body. It is essential to include a fixed amount of the active ingredient in the composition to ensure that the patient receives a therapeutically effective dose. The content of the scopolamine salt and/or its hydrate in the composition of the present invention is 0.5 to 10 mass %, preferably 1 to 8 mass %, more preferably 3 to 6 mass % with respect to the total composition. Doses less than 0.5% by weight may result in an insufficient therapeutic effect, while doses greater than 10% by weight may be economically disadvantageous.

The composition of the present invention contains polyvinylpyrrolidone to improve the chemical stability of scopolamine. The weight average molecular weight of the polyvinylpyrrolidone used in the composition of the present invention is not particularly limited, although the weight average molecular weight of the polyvinylpyrrolidone generally used ranges from several thousand to several million One or more kinds of this polyvinylpyrrolidone can be used.

The content of polyvinylpyrrolidone in the composition of the present invention is in the range of 0.3 to 12 mass %, preferably 0.5 to 10 mass %, and more preferably 1 to 8 mass % with respect to the total composition. When the content is less than 0.3% by mass, sufficient chemical stability improving effect may not be obtained, whereas when the content is more than 12% by mass, the physical properties of the composition may be adversely affected, which is not favorable. The mass ratio of the polyvinylpyrrolidone to the scopolamine salt and/or its hydrate is preferably less than 2 because the weight ratio of the polyvinylpyrrolidone to the scopolamine salt and/or its hydrate may adversely affect the uniformity of the composition.

The composition of the present invention contains a base to make the scopolamine salt and/or its hydrate a free base. The base type is not particularly limited, and examples thereof include amine compounds, ammonia, hydroxides of alkali metals, and the like. Among these bases, an amine compound is favorable in terms of chemical stability.

The amine compound may be any of a primary amine, a secondary amine, and a tertiary amine. Examples of primary amine include methylamine, ethylamine, dodecylamine, and the like. Examples of secondary amine include dimethylamine, diethylamine, N-methylethanamine, and the like. Examples of the tertiary amine include, but are not limited to, N,N-diethylmethylamine, tributylamine, N,N-dimethyl-p-toluidine, N,N-diethyl-p-toluidine, methyl methacrylate/butyl methacrylate/dimethylaminoethyl methacrylate copolymer, and the like. At least one of these amine compounds can be used. A copolymer of methyl methacrylate, butyl methacrylate, and dimethylaminoethyl methacrylate is favorable among these amine compounds. Examples of the alkali metal hydroxide include but are not limited to sodium hydroxide and potassium hydroxide.

The content of the base in the composition of the present invention is in the range of 0.3 to 10 mass %, preferably 0.5 to 8.5 mass %, and more preferably 0.9 to 7.5 mass % with respect to the entire composition. Concentrations below 0.3 mass % may not provide adequate absorption into the living body, while concentrations above 10 mass % may adversely affect chemical stability.

The method for producing the composition of the present invention is not particularly limited, and for example, the essential components may be mixed by stirring. If necessary, a solvent such as an ethyl acetate or methanol may be added.

The above-described composition of the present invention can be formulated in place of the active ingredients and the like of conventional pharmaceutical compositions. The dosage form of the composition of the present invention includes, but is not limited to, oral preparations, injections, external preparations, and the like. Among these dosage forms, an external preparation that can be conveniently administered is favorable.

Examples of external preparations include, but are not limited to, dusting powders, lotions, ointments, creams, sprays, liquids, patches, aerosols, rectal suppositories, ear drops, eye drops, nasal drops, inhalants, and the like. Among these, the patch is favorable because complicated operations such as wiping and dosage adjustment are not required, the blood concentration of the active ingredient can be stably maintained, the effective time is long, and the administration can be easily interrupted by peeling at the onset of an adverse event.

Examples of the patch include a matrix type and a reservoir type. The composition of the present invention may be either a matrix type or a reservoir type, but a matrix type is preferred because formulation design is easy and manufacturing costs can be reduced.

A matrix type patch comprises a support, a drug-containing adhesive layer, and a release liner (hereinafter referred to as the "patch of the present invention").

The drug-containing adhesive layer may contain the composition of the present invention but preferably also contains a base component. The base component used in this drug-containing adhesive layer is not particularly limited, but an adhesive component generally used in patches such as a rubber-based adhesive component, an acrylic adhesive component, and a silicone-based adhesive component is favorable, an acrylic adhesive component is particularly favorable, and a non-polar acrylic adhesive component and a hydroxyl group-containing acrylic adhesive component are more favorable. At least one of these base components may be used.

The acrylic adhesive component is a polymer or a copolymer containing at least one (meth) acrylic acid ester.

The non-polar type acrylic adhesive component does not have a functional group on the side chain in the monomer structural unit, and examples thereof include alkyl (meth) acrylate polymer or a copolymer, an alkyl (meth) acrylate/vinyl acetate copolymer, and specific examples thereof include, but are not limited to, acrylic acid-2-ethylhexyl-methacrylate-2-ethylhexyl-dodecyl methacrylate copolymer, acrylic acid-2-ethylhexyl-vinyl acetate copolymer, methyl methacrylate/butyl methacrylate/dimethylaminoethyl methacrylate copolymer, and the like.

The acrylic adhesive component of the hydroxyl group-containing type is a polymer or a copolymer having as a constituent monomer at least one type of (meth) acrylic ester having a free hydroxyl group in a side chain in a monomer constituent unit, and includes, for example, a copolymer including a hydroxyalkyl (meth) acrylic ester, and specifically includes, but is not limited to, an acrylic acid-2-ethylhexyl/acrylic acid hydroxylethyl/vinyl acetate copolymer, an acrylic acid-2-ethylhexyl/vinyl pyrrolidone/acrylic acid hydroxylethyl/vinyl acetate copolymer, an acrylic acid-2-ethylhexyl/acrylic acid hydroxylethyl/vinyl acetate copolymer, an acrylic acid-2-ethylhexyl/acrylic acid hydroxylethyl/acrylic acid glycidyl/vinyl acetate copolymer, an acrylic acid-2-ethylhexyl/vinyl acetate/acrylic acid-2-hydroxyethyl copolymer, and an acrylic acid-2-ethylhexyl/vinyl acetate/acrylic acid-2-hydroxyethyl/glycidyl methacrylate copolymers.

The content of the base component in the drug-containing adhesive layer is 60 to 98.9 mass %, preferably 63 to 98 mass %, and more preferably 66 to 96 mass % with respect to the entire drug-containing adhesive layer taking into account the formation of the drug-containing adhesive layer and sufficient drug releasabilities. When the content is less than 60% by mass, physical properties such as anchoring ability as a patch may deteriorate, and when the content is more than 98.9%, the active ingredient and other additives may not be sufficiently blended, which may be undesirable.

The drug-containing adhesive layer may contain an absorption promoter, if necessary. The absorption promoter may be any of the compounds which have conventionally been found to promote absorption in transdermal administration, and examples thereof include fatty acids such as lauric acid, oleic acid, isostearic acid, isopropyl myristate, octyldodecyl myristate, glycerol oleic acid monoester, hexyldecyl isostearate, and esters thereof, alcohols such as oleyl alcohol, propylene glycol, polyethylene glycol monooleate and esters or ethers thereof, sorbitan esters or ethers, such as sorbitan sesquioleate, polyoxyethylene sorbitan monooleate, sorbitan monolaurate, sorbitan monooleate, phenol ethers such as polyoxyethylene nonylphenyl ether, polyoxyethylene octylphenyl ether, ionic surfactants such as castor oil or hardened castor oil, oleoyl sarcosine, lauric dimethyl aminoacetic acid betaine, and sodium lauryl sulfate, nonionic surfactants such as polyoxyethylene oleyl ether, polyoxyethylene lauryl ether, alkyl methyl sulfoxide such as dimethyl sulfoxide and decyl methyl sulfoxide, azacycloalkanes such as 1-dodecyl azacycloheptane-2-one and 1-geranyl azacycloheptane-2-one, and pyrrolidones excluding polyvinylpyrrolidone.

The support used in the patch of the present invention is not particularly limited, but for example, a support that is impermeable to drugs and elastic or non-elastic can be used. Examples of the support include a synthetic resin film or sheet such as polyethylene, polypropylene, polybutadiene, ethylene-vinyl acetate copolymer, polyvinyl chloride, polyester (polyethylene terephthalate, and the like), nylon, polyurethane, or a laminate, a porous body, a foam, paper, a woven fabric, a non-woven fabric, and the like, thereof.

The release liner used in the patch of the present invention is not particularly limited, but for example, a release liner impermeable to a drug can be used. Examples of the release liner include a film made of a polymer material such as polyethylene, polypropylene, or polyester, a film on which aluminum is vapor-deposited, and a paper on which silicone oil, or the like, is applied. Among them, a polyester film is favorable in terms of workability and low cost without permeation of an active component, and a polyethylene terephthalate (PET) film is particularly favorable. Further, a laminate film formed by laminating a plurality of materials may be used as the release liner.

The patch of the present invention is stored in packaging material until use. The packaging material used for the patch of the present invention is not particularly limited, and examples thereof include plastic films, metal (e.g., aluminum) laminated plastic films, metal vapor-deposited plastic films, ceramic (e.g., silicon oxide), vapor-deposited plastic films, metal foils such as aluminum foils, metals such as stainless steel, glass, and the like. Because of production cost and the like, it is favorable to use a metal laminated plastic film, a metal vapor-deposited plastic film, and the like.

If necessary, to control the percutaneous absorption of the active ingredient of the patch of the present invention, a release-regulating membrane may be added to the skin application side of the drug-containing adhesive layer, or an adhesive layer may be added to the skin application side to apply the adhesive layer to the skin.

The patch according to the present invention described above comprises a support, a drug-containing adhesive layer, and a release liner, wherein the support has a thickness of 1 to 1000 μm, preferably 10 to 700 μm, the drug-containing adhesive layer has a thickness of 10 to 200 μm, preferably 30 to 150 μm, and the release liner has a thickness of 1 to 500 μm, preferably 10 to 200 μm.

The patch of the present invention can be produced in accordance with a known method for producing a patch. Favorable methods for producing the patch of the present invention include, for example, the following methods.

<Method 1>

A patch is obtained by spreading, on a release liner or support, a solution obtained by dissolving a salt of scopolamine, which is an active ingredient, and/or a hydrate thereof, a base, polyvinylpyrrolidone, a base component, and an absorption promoter, if necessary, in an organic solvent such as ethyl acetate or methanol or a mixed solvent thereof, evaporating the organic solvent in the solution to form a drug-containing adhesive layer, and then adhering the support or the release liner.

<Method 2>

A patch is obtained by heating and dissolving a salt of scopolamine, which is an active ingredient, and/or a hydrate thereof, a base, polyvinylpyrrolidone, a base ingredient, and, if necessary, an absorption promoting agent and the like, spreading the melt on a release liner or support to form a drug-containing adhesive layer, and then adhering the support or release liner.

EXAMPLES

Production examples are shown below to explain the present invention more specifically. However, the present invention is not limited to these production examples, and various modifications can be made without departing from the technical idea of the present invention.

Production Example 1

Scopolamine hydrobromide hydrate, isopropyl myristate, and dodecylamine were dissolved in a mixture of ethyl acetate and methanol according to the blending ratios shown in Table 1, and acrylic adhesive components (trade name: DURO-TAK 87-4287, manufactured by Henkel) were added and mixed and stirred to obtain a homogeneous solution. Next, this solution was spread on a release film using a doctor-knife coating machine so that the thickness after drying was 100 μm, dried to form a drug-containing adhesive layer, and then adhered to a support. Then, it was cut to the desired size to obtain a patch

Production Example 2

A patch was obtained in the same manner as in Production Example 1, except that diethylamine was added in place of dodecylamine according to the blending ratios described in Table 1 so that the amount of scopolamine free base was equivalent to that in Production Example 1.

Production Example 3

A patch was prepared in the same manner as in Production Example 1, except that a copolymer of methyl methacrylate, butyl methacrylate, and dimethylaminoethyl methacrylate (trade name: EUDRAGIT EPO, manufactured by Evonik) was added in place of dodecylamine according to the blending ratios shown in Table 1 so that the amount of scopolamine free base was equivalent to that in Production Example 1.

Production Example 4

A patch was obtained in the same manner as in Production Example 1, except that sodium hydroxide was added in place of dodecylamine, and further polyvinylpyrrolidone (trade name: Kollidon30, manufactured by BASF SE) was added in accordance with the blending ratios described in Table 1 so that the amount of scopolamine free base was equivalent to that in Production Example 1.

Production Example 5

A patch was obtained in the same manner as in Production Example 1, except that Eudragit EPO was added in place of dodecylamine, and further polyvinylpyrrolidone was added according to the blending ratios described in Table 1 so that the amount of scopolamine free base was equivalent to that in Production Example 1.

Production Example 6

Scopolamine hydrobromide hydrate, Eudragit EPO, and polyvinylpyrrolidone were dissolved in a mixture of ethyl acetate and methanol in accordance with the blending ratio described in Table 1, and KURO-TAK 87-4287 was added thereto and mixed and stirred to obtain a homogeneous solution. Next, this solution was spread on a release film using a doctor-knife coating machine so that the thickness after drying was 100 μm, dried to form a drug-containing adhesive layer, and then adhered to a support. Then, it was cut to the desired size to obtain a patch.

Production Example 7

A patch was obtained in the same manner as in Production Example 6, except that the amount of polyvinyl pyrrolidone was increased according to the blending amount shown in Table 1

Production Example 8

Scopolamine hydrobromide hydrate, isopropyl myristate, Eudragit EPO, and polyvinylpyrrolidone were dissolved in a mixture of ethyl acetate and methanol in accordance with the blending ratios described in Table 1, and KURO-TAK 87-4287 was added and mixed and stirred to obtain a homogeneous solution. Next, this solution was spread on a release film using a doctor-knife coating machine so that the thickness after drying was 100 μm, dried to form a drug-containing adhesive layer, and then adhered to a support. Then, it was cut to the desired size to obtain a patch.

Production Example 9

Scopolamine hydrobromide hydrate, isopropyl myristate, Eudragit EPO, and polyvinylpyrrolidone were dissolved in a mixture of ethyl acetate and methanol in accordance with the blending ratios described in Table 1, and KURO-TAK 87-4287 was added and mixed and stirred to obtain a homogeneous solution. Next, using a doctor-knife coating machine, the solution was spread on a release film so that the thickness after drying became 50 μm, dried to form a drug-containing adhesive layer, and then adhered to a support. Then, it was cut to the desired size to obtain a patch.

Production Example 10

A patch was obtained in the same manner as in Production Example 9, except that the amount of isopropyl myristate was increased according to the blending amounts shown in Table 1.

Production Example 11

A patch was obtained in the same manner as in Production Example 1, except that sodium hydroxide was added in place of dodecylamine according to the blending ratio described in Table 1 so that the amount of scopolamine free base was equivalent to that in Production Example 1.

Production Example 12

A patch was obtained in the same manner as in Production Example 6, except that polyvinyl pyrrolidone was not added according to the blending ratio shown in Table 1.

Production Example 13

A patch was obtained in the same manner as in Production Example 1, except that dodecylamine was not added according to the blending ratios shown in Table 1.

TABLE 1

| | Prod. Ex. 1 | Prod. Ex. 2 | Prod. Ex. 3 | Prod. Ex. 4 | Prod. Ex. 5 | Prod. Ex. 6 | Prod. Ex. 7 | Prod. Ex. 8 | Prod. Ex. 9 | Prod. Ex. 10 | Prod. Ex. 11 | Prod. Ex. 12 | Prod. Ex. 13 |
|---|---|---|---|---|---|---|---|---|---|---|---|---|---|
| scopolamine hydrobromide hydrate | 3 | 3 | 3 | 3 | 3 | 3 | 3 | 3 | 6 | 6 | 3 | 3 | 3 |
| acrylic adhesive component*[1] | 91 | 91.6 | 90.5 | 89.3 | 88 | 95 | 91 | 81 | 71 | 66 | 91.8 | 96 | 92 |
| sodium hydroxide | — | — | — | 0.2 | — | — | — | — | — | — | 0.2 | — | — |
| dodecylamine | 1 | — | — | — | — | — | — | — | — | — | — | — | — |
| diethylamine | — | 0.4 | — | — | — | — | — | — | — | — | — | — | — |
| methyl-methacrylate/butyl methacrylate/dimethylaminoethyl methacrylate copolymer*[2] | — | — | 1.5 | — | 1.5 | 1 | 1 | 2 | 5 | 5 | — | 1 | — |
| polyvinylpyrrolidone | — | — | — | 2.5 | 2.5 | 1 | 5 | 4 | 8 | 8 | — | — | — |
| isopropyl myristate | 5 | 5 | 5 | 5 | 5 | — | — | 10 | 10 | 15 | 5 | — | 5 |

*[1]DURO-TAK 87-4287
*[2]EUDRAGIT EPO

Test Example 1

Chemical Stability Test 1

Each of the patches obtained in Production Examples 1 to 13 was packed in a bag of a composite film (an aluminum-laminated film of the innermost layer heat-sealed PET, manufactured by Maywapax), stored in a thermo-hygrostat (temperature: 60° C., CSH-110, manufactured by Tabai Espec) for three days or 28 days, and the amount of optical isomer, which was major decomposition products, was measured. The three sheets of patches, with the liners removed, were placed in a 10 mL centrifuge tube, 1 mL of tetrahydrofuran and 0.5 mL of methanol were added, and were shaken for 10 minutes to dissolve the paste completely. 1 mL of water was added to this liquid, and the mixture was shaken for 10 minutes to flocculate and precipitate the adhesive base component completely. The supernatant liquid was used as the sample solution, and the content was measured by high-performance liquid chromatography (wavelength: 210 nm). The amounts of optical isomers after storage measured by the method are shown in Tables 2 and 3.

Test Example 2

Chemical Stability Test 2

Each of the patches obtained in Production Examples 1 to 13 was filled in a bag of a composite film (an aluminum-laminated film of the innermost layer heat-sealed PET, manufactured by Maywapax), stored in a thermo-hygrostat (temperature: 60° C., CSH-110, manufactured by Tabai Espec) for three days or 28 days, and the amount of aposcopolamine, which was the main decomposition product, was measured. Three sheets of patches, with the liners removed, were placed in a 10 mL centrifuge tube, 1 mL of tetrahydrofuran and 0.5 mL of methanol were added, and were shaken for 10 minutes to dissolve the paste completely. 1 mL of water was added to this liquid, and the mixture was shaken for 10 minutes to flocculate and precipitate the adhesive base component completely. The supernatant liquid was used as the sample solution, and the content was measured by high-performance liquid chromatography (wavelength: 220 nm). The amounts of aposcopolamine after storage measured by the method are shown in Tables 2 and 3.

Test Example 3

Release Test

For each patch obtained in Production Examples 5, 8, 9, 10, and 13, the release rate of scopolamine from the patch was measured. Each patch was cut with a leather punch of 15 mm in diameter, affixed to filter paper, covered with a cover tape, cut with a leather punch of 23 mm in diameter so that the test piece was at the center, and a release test was performed using a percutaneous absorption test apparatus (TRANS VIEW $C_{12}$, manufactured by Cosmidi Pharmaceutical). In the operation of the percutaneous absorption test apparatus, a stirrer was placed in the diffusion cell, the test piece and the diffusion cell hole were set together, and a collar and a cap were attached thereon. A test liquid kept at 32° C. (3.40 g of potassium dihydrogen phosphate and 3.55 g of anhydrous disodium hydrogen phosphate dissolved in 1000 mL of water) was injected into the receiver tank of the diffusion cell. The diffusion cell was placed in a heat block thermostatic chamber (temperature: 32±2° C.). The sample solution was sampled after 24 hours. The amount was measured by high-performance liquid chromatography (measurement wavelength: 210 nm). The release rate of scopolamine after 24 hours in each patch measured by the method is shown in Table 4.

Test Example 4

Combination Study

A drug solution containing scopolamine free base and polyvinylpyrrolidone in a blending ratio of 1:0, 2:1, 1:1, 1:2 was prepared (Production Examples 14 to 17). Each drug solution thus obtained was taken into a 10 mL centrifuge tube, stored in a hot-air dryer (temperature: 70° C., LC 110, manufactured by Tabai Espec) for one day, and the amounts of optical isomers and aposcopolamine after storage were measured by high-performance liquid chromatography (measuring wavelengths: 210 nm and 220 nm). The amounts of optical isomers and the aposcopolamine after storage measured by the method are shown in Table 5.

TABLE 2

| | Amount of each decomposition product (%, 60° C. 3 days later) | | |
|---|---|---|---|
| | Optical isomer | aposcopolamine | total |
| Prod. Ex. 11 | 8.88 | 0.87 | 9.75 |
| Prod. Ex. 1 | 0.50 | 0.17 | 0.67 |
| Prod. Ex. 2 | 4.80 | 0.70 | 5.50 |
| Prod. Ex. 3 | 0.29 | 0.46 | 0.75 |
| Prod. Ex. 4 | 1.61 | 0.51 | 2.12 |
| Prod. Ex. 5 | 0.15 | 0.31 | 0.46 |

TABLE 3

| | Amount of each decomposition product (%, 60° C. 28 days later) | | |
|---|---|---|---|
| | Optical isomer | aposcopolamine | total |
| Prod. Ex. 12 | 0.33 | 1.67 | 2.00 |
| Prod. Ex. 6 | 0.18 | 0.95 | 1.13 |
| Prod. Ex. 7 | 0.15 | 0.86 | 1.01 |
| Prod. Ex. 8 | 0.54 | 0.86 | 1.40 |
| Prod. Ex. 9 | 0.62 | 0.94 | 1.56 |
| Prod. Ex. 10 | 0.46 | 0.90 | 1.36 |

TABLE 4

| | Release rate (%, 24 hours later) |
|---|---|
| Prod. Ex. 13 | 3.4 |
| Prod. Ex. 5 | 54.8 |
| Prod. Ex. 6 | 38.6 |
| Prod. Ex. 7 | 35.7 |
| Prod. Ex. 8 | 82.0 |
| Prod. Ex. 9 | 80.0 |
| Prod. Ex. 10 | 82.2 |

TABLE 5

| | Scopolamine | Amount of each decomposition product (%, 70° C. 1 day later) | | |
|---|---|---|---|---|
| | free base:poly-vinylpyrrolidone | Optical isomer | aposcopolamine | total |
| Prod. Ex. 14 | 1:0 | 6.93 | 12.81 | 19.74 |
| Prod. Ex. 15 | 2:1 | 2.28 | 5.67 | 7.95 |
| Prod. Ex. 16 | 1:1 | 1.64 | 4.37 | 6.01 |
| Prod. Ex. 17 | 1:2 | 1.17 | 3.24 | 4.41 |

Compared with Production Example 11 (free base formation using sodium hydroxide), the amounts of optical isomers and aposcopolamine are low in Production Examples 1 (free base formation using dodecylamine), 2 (free base formation using diethylamine), Production Example 2 (free base formation using diethylamine), and Production Example 3 (free base formation using Eudragit EPO), in which an amine compound is used as a base for making scopolamine a free base. The above results have revealed that using an amine compound as a base for making a scopolamine salt and/or its hydrate a free base effectively improves the chemical stability of scopolamine.

In the blending test, blending polyvinylpyrrolidone (Production Examples 15 to 17) decreased the optical isomer and aposcopolamine compared to when polyvinylpyrrolidone was not blended (Production Example 14). As the ratio of polyvinylpyrrolidone to scopolamine free base increased, optical isomers and apospolamine decreased. The above results demonstrated that adding polyvinylpyrrolidone effectively improves the chemical stability of scopolamine.

Compared with Production Example 11, the amounts of optical isomers and aposcopolamine are smaller in Production Example 4, where polyvinylpyrrolidone is blended. Further, compared to Production Example 3, the amounts of optical isomers and aposcopolamine are smaller in Production Example 5, where polyvinylpyrrolidone is blended. Further, in comparison with Production Example 12, the amounts of optical isomers and aposcopolamine are smaller in Production Examples 6 and 7 in which polyvinylpyrrolidone is blended. The above results show that adding polyvinylpyrrolidone effectively improves the chemical stability of scopolamine even when a patch is used as the dosage form.

Production Example 8 is a formulation in which the amount of Eudragit EPO is increased so that the amount of scopolamine free base is twice as large as that in Production Example 12, and chemical stability is made under more severe conditions than that in Production Example 12. Further, Production Examples 9 and 10 are formulations in which the amounts of scopolamine hydrobromide hydrate and Eudragit EPO are increased so that the amount of scopolamine free base is 4.7 times that in Production Example 12, and the chemical stability is made under more severe conditions than in Production Example 12. Under these conditions, compared with Production Example 12, although the addition of polyvinylpyrrolidone could not suppress the increase in the amount of optical isomers, the amount of aposcopolamine decreased, and the total amount of decomposition products also decreased. The above results have shown that the addition of polyvinylpyrrolidone effectively improves the chemical stability of scopolamine even under severe conditions of chemical stability.

The release rate after 24 hours is higher in Production Examples 5, 6, 7, 8, 9, and 10 than in Production Example 13. The above results showed that using an amine compound as a base and scopolamine hydrobromide as a free base effectively improves absorption into a living body.

INDUSTRIAL APPLICABILITY

As described above, the composition of the present invention is a pharmaceutical composition produced by including polyvinylpyrrolidone and a base in a composition containing a scopolamine salt and/or a hydrate thereof and is a novel pharmaceutical composition having high absorption into the living body and excellent chemical stability of scopolamine. The composition of the present invention can effectively and continuously utilize the pharmacological effect of scopolamine.

The invention claimed is:

1. A pharmaceutical composition comprising
3 to 6 mass % of scopolamine hydrobromide hydrate,
4 to 8 mass % of polyvinylpyrrolidone,
10 to 15 mass % of isopropyl myristate,
2 to 5 mass % of a methyl methacrylate-butyl methacrylate-dimethylaminoethyl methacrylate copolymer, and
66 to 81 mass % of an acrylic adhesive.

2. The pharmaceutical composition according to claim 1, wherein a content of the scopolamine hydrobromide hydrate is 6 mass % with respect to a total mass of the pharmaceutical composition.

3. The pharmaceutical composition according to claim 1, wherein a content of the polyvinylpyrrolidone is 8 mass % with respect to a total mass of the pharmaceutical composition.

4. The pharmaceutical composition according to claim 1, wherein a content of the methyl methacrylate-butyl methacrylate-dimethylaminoethyl methacrylate copolymer is 5 mass % with respect to a total mass of the pharmaceutical composition.

5. A matrix-type patch comprising a support, a drug-containing adhesive layer, and a release liner, wherein the drug-containing adhesive layer contains the pharmaceutical composition according to claim 1.

6. The pharmaceutical composition according to claim 1, wherein the mass ratio of the scopolamine hydrobromide hydrate to the polyvinyl pyrrolidone is 1:1 to 1:2.

* * * * *